United States Patent [19]

Ellison et al.

[11] Patent Number: Plant 7,155

[45] Date of Patent: Feb. 13, 1990

[54] ASPARAGUS PLANT NAMED 'JERSEY PRINCESS'

[75] Inventors: J. Howard Ellison, Milltown; John J. Kinelski, Princeton, both of N.J.

[73] Assignee: Rutgers University, New Brunswick, N.J.

[21] Appl. No.: 280,750

[22] Filed: Dec. 7, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

A female asparagus plant selected for, earliness of production vigor and high yield, disease resistance to rust (*Puccinia asparagi*), tolerance to root rot (*Fusarium oxysporum*) and crown rot (*F. moniliforme*) and numerous extremely tall summar stalks, reaching a height of 2.7 meters.

1 Drawing Sheet

BACKGROUND OF THE INVENTION

Continuing a long series of developmental efforts to produce an asparagus plant, which is disease resistant, has earliness of production, vigor and high yield, the instant variety was selected from a cross between a previously developed hybrid, known as "Inez", U.S. Plant Pat. No. 5,546, and an unpatented variety which we have designated No. 104B.

SUMMARY OF THE INVENTION

Some of the particularly noticeable aspects of improvement which we have found as a result of this development, is that the number of cladodes per node, which is 13, is two or three times the usual number for other plants.

When the combination of the large number of tall stalks is considered, the same provides a great photosynthetic surface for the elaboration of carbohydrates. This large green top provides further for the storage of large quantities of reserves in the root system, which are needed for the high yield of spears during the following spring.

This particular variety which we have caused to be asexually reproduced by crown division and tissue culture, discloses that it comes true in successive generations with the characteristics of resistance to the various diseases and tolerance to root rot which has been before described and is maintained therein.

It should be noted that as is true of one of the parent varieties, this particular variety which we designate as "Jersey Princess", and in our records as 353H, is of the female sex as will be understood from the name and it does in fact carry the characteristics mentioned to make the same a valuable cloned variety and enable the farmer to grow clones of the variety where standard cultivars are not normally grown profitably.

It should be noted further that our new variety "Jersey Princess" will be valuable as a cloned variety producing an extremely high yield of spears, along with the tolerance to rust (*Puccinia asparagi*), root rot (*Fusarium oxysporum*) and crow rot (*F. moniliforme*).

The variety has been grown in a field in which other known varieties have been experimentally produced and reproduced as well. A number of the varieties which we have developed over time have likewise been developed as a result of our program of improvement in asparagus plants in general.

In this development as well as in other instances, and in patients which have been granted as for a parent of the instant variety, U.S. Plant Pat. No. 5,546, known as "Inez", have enabled us to accumulate comparative data and in the present instance, in reference to this variety, it is summarized in the following table which sets forth some of the information which makes it possible for us to identify the new plant and compare it with other varieties.

BRIEF DESCRIPTION OF THE DRAWING

In the accompanying drawing we disclose in FIG. 1 a typical stalk of our new variety with the dimensions and other elements indicated thereon in black and white.

Figure 2:
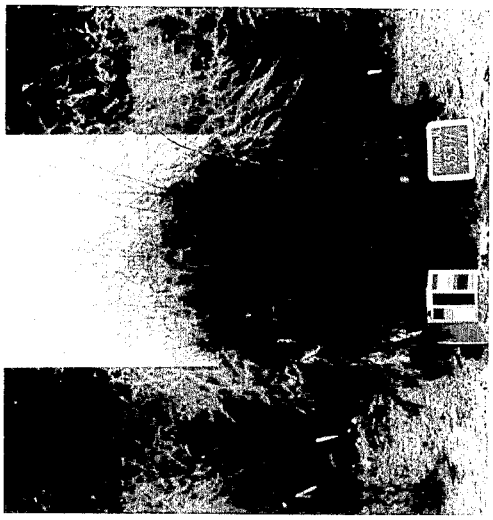
In FIG. 2 we show in color as nearly as possible representative of a typical plant, of the plants of our new variety with the color compared by us to the Munsell Limit Color Cascade and the disclosure is as nearly accurate as can be reproduced in an illustration of this kind, the photo having been taken under normal daylight conditions in the field where grown.
Figure 1:
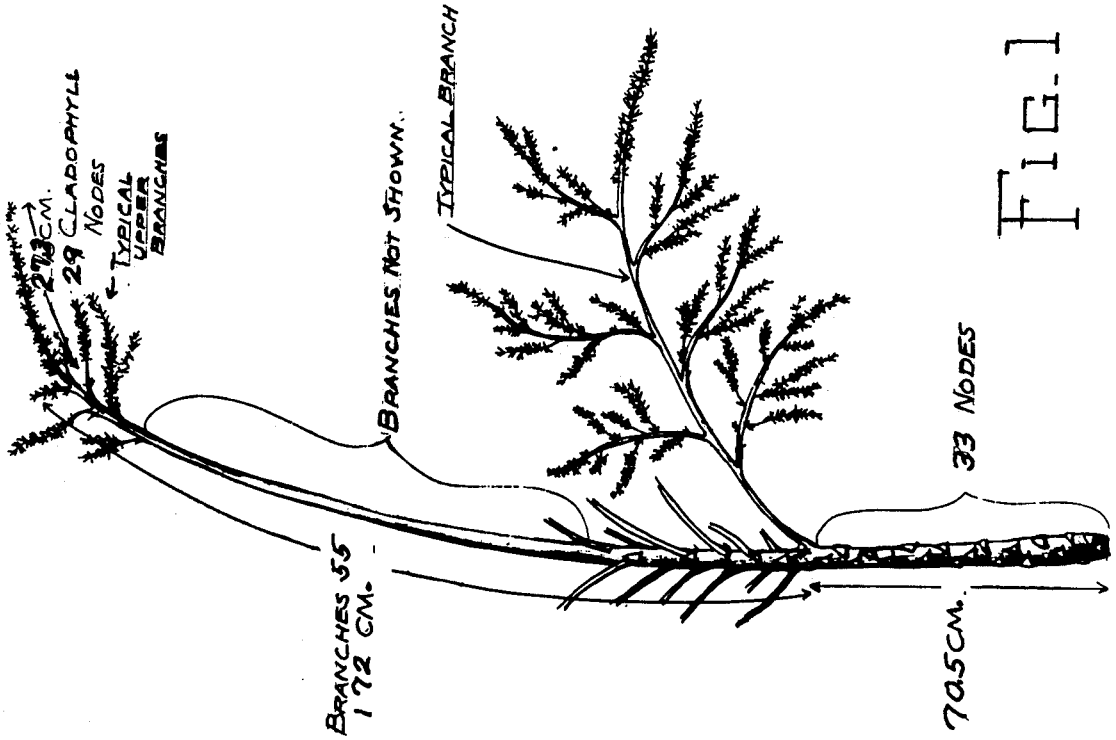

ASPARAGUS PLANT DATA
ASPARAGUS PLANT - "JERSEY PRINCESS"

| | |
|---|---|
| Stalk Data | |
| Number of nodes below first branch | 33 |
| Number of cm from crown to first branch | 70.5 |
| Number of branches | 55 |
| Number cm between first and last branch | 172 |
| Internode length in cm between branches | 3.13 |
| Number of cladophyll nodes beyond last branch | 29 |
| Number of cm beyond last branch | 27.3 |
| Internode length in cm beyond last branch | 0.94 |
| Largest stalk diameter in mm | 20 |
| Mean diameter of three largest stalks in mm | 18 |
| Number of stalks | 66 |
| Stalk vigor index (No. × (Mean Diam)) | 21384 |
| Mature stalk color, bloom removed. Color No. | 21.5–13 |
| Inches to 1st branch highest headed stalk in cm | 70.5 |
| Length of highest headed stalk in cm | 270 |
| Flower Data | |
| Petal tip (yellow) Color No. | 25.6–3 |
| Petal base (green) Color No. | 22–10 |
| Flower length mm | 4.43 |
| Flower width at midpoint mm | 2.38 |
| Cladophyll Data | |
| Number per node | 13.3 |
| Length mm | 20.0 |
| Width mm | 0.127 |

-continued

| ASPARAGUS PLANT DATA<br>ASPARAGUS PLANT - "JERSEY PRINCESS" | |
|---|---|
| Fruit Data | |
| Weight of 100 fruit (g) | 30.4 |
| Water displacement of 100 fruit (ml) | 36.0 |
| Number of seed per 100 fruit | 342 |
| Weight of seed per 100 fruit (g) | 9.3 |
| Mean weight per seed | 0.0272 |
| Water displacement of seed of 100 fruit (ml) | 11.0 |
| Mature fruit color No. | 33-12 |

We have also accumulated information to compare the yield of asparagus clones, and in this instance we have selected one of our clones, No. 12 to compare with the instant variety "Jersey Princess".

According to our records which represent data accumulated over several years from 1984 to 1988, the fact that the mean pounds of marketable jumbo spears (spears 16 mm and greater in diameter) for clone No. 12 is 2.02, as compared with 2.82 pounds for the instant variety.

Comparing production of marketable spears (spears 10 mm and greater in diameter) of the respective plants, we have established that the mean pounds produced for clone No. 12 is 2.35, whereas the mean for "Jersey Princess" is even more strikingly greater, specifically 4.06 pounds.

It should be pointed out that the foregoing refers to the production from each plant of the plants for which the data was assembled.

The data set forth establishes to our satisfaction that "Jersey Princess" is a substantially better producer as it yields more pounds of stalk per plant.

In a comparable analysis, maximum marketable yield of hybrid plants in New Jersey, where the instant variety was developed and grown, is approximately 0.60 pounds per plant per year indicating that "Jersey Princess" the subject of the current disclosure, yields approximately six times as much as the usual plant.

We claim:

1. A new and distinct variety of asparagus plant as herein shown and described, distinguished particularly as to novelty by its unique combination of predominantly female characteristics, producing high yield, having tolerance to rust (*Puccinia asparagi*), root rot (*Fusarium oxysporum*) and crown rot (*F. moniliforme*), and substantially greater market yield as compared with hybrid plants, these characteristics enabling growth of the plant where standard susceptible cultivars cannot be grown profitably.

* * * * *